United States Patent
Fronabarger et al.

(10) Patent No.: US 7,145,016 B1
(45) Date of Patent: Dec. 5, 2006

(54) NITROBENZODIFUROXAN COMPOUNDS, INCLUDING THEIR SALTS, AND METHODS THEREOF

(75) Inventors: John William Fronabarger, Sun Lakes, AZ (US); Michael E. Sitzmann, Adelphi, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 370 days.

(21) Appl. No.: 10/652,080

(22) Filed: Aug. 28, 2003

(51) Int. Cl.
*C07D 271/12* (2006.01)
(52) U.S. Cl. .................................. 548/126
(58) Field of Classification Search ............. 548/125
See application file for complete search history.

(56) References Cited

U.S. PATENT DOCUMENTS

| | | | |
|---|---|---|---|
| 3,163,561 A | 12/1964 | Hardy et al. ............... | 136/127 |
| 4,529,801 A | 7/1985 | Norris ...................... | 548/126 |
| H476 H | 6/1988 | Norris ...................... | 548/126 |
| 4,754,040 A | 6/1988 | Chafin et al. .............. | 548/126 |
| 5,039,812 A | 8/1991 | Norris ...................... | 548/126 |
| H1078 H | 7/1992 | Norris et al. .............. | 548/126 |
| 5,136,041 A | 8/1992 | Weber ...................... | 548/126 |
| 5,149,818 A | 9/1992 | Christian et al. .......... | 548/126 |

*Primary Examiner*—Kamal A. Saeed
(74) *Attorney, Agent, or Firm*—Fredric J. Zimmerman

(57) ABSTRACT

A nitrobenzodifuroxan compound having the chemical structure of:

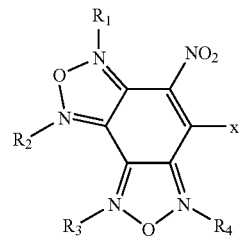

wherein two of the $R_1$, $R_2$, $R_3$ and $R_4$ comprise oxygen or are absent, and only one of $R_1$ or $R_2$ is present, and only one of $R_3$ and $R_4$ is present, and wherein x is hydrolyzed or hydrolyzable. The salt of the hydroxynitrobenzodifuroxan of this compound is useful in explosive compositions.

13 Claims, 1 Drawing Sheet

FORM B

FORM A

NITROBENZODIFUROXAN COMPOUNDS, INCLUDING THEIR SALTS, AND METHODS THEREOF

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefore.

BACKGROUND OF THE INVENTION

1. Field of the Invention

The present invention provides nitrobenzodifuroxan compounds, such as methoxynitrobenzodifuroxan and hydroxynitrobenzodifuroxan, and its salts.

2. Brief Description of the Related Art

Toxicity and environmental concerns are present with the use of lead azide and lead styphnate, particularly when used in ordnance items such as initiating materials in primary explosives. Replacement materials for lead azide and lead styphnate are optimal with high autoignition temperatures of at least 200° C. or higher.

In example 11 of U.S. Pat. No. 3,163,561 to Hardy et al., trichlorotrinitrobenzene and sodium azide are used as reagents to make benzotrifuroxan. In U.S. Pat. No. 5,149,818 to Christian et al., an insensitive explosive material of aminonitrobenzodifuroxan is formed. However, neither of these patents disclose a formation of a sensitive nitrobenzodifuroxan explosive composition.

There is a need in the art to provide initiating materials employing non-heavy metal primary explosives that are sensitive explosives with high autoignition temperatures. The present invention addresses this and other needs.

SUMMARY OF THE INVENTION

The present invention includes a nitrobenzodifuroxan compound having the chemical structure of:

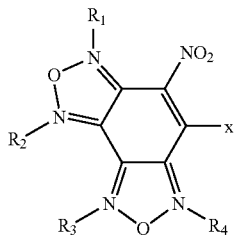

wherein $R_1$, $R_2$, $R_3$ and $R_4$ comprise oxygen or are absent, for a total of two oxygen atoms, and only one of $R_1$ or $R_2$ is present, and only one of $R_3$ and $R_4$ is present, and wherein x is a hydrolyzed or hydrolyzable substituent. Preferred compounds include methoxynitrobenzodifuroxan and hydroxynitrobenzodifuroxan.

The present invention also includes salts of hydroxynitrobenzodifuroxan, including Form A and Form B salts.

Additionally, the present invention includes a process for producing hydroxynitrobenzodifuroxan comprising the steps of providing a hydrolyzable nitrobenzodifuroxan and hydrolyzing the nitrobenzodifuroxan effective to form hydroxynitrobenzodifuroxan, with a further step of forming the salt of the hydroxynitrobenzodifuroxan.

DETAILED DESCRIPTION OF THE PREFERRED EMBODIMENT

Figure 1:
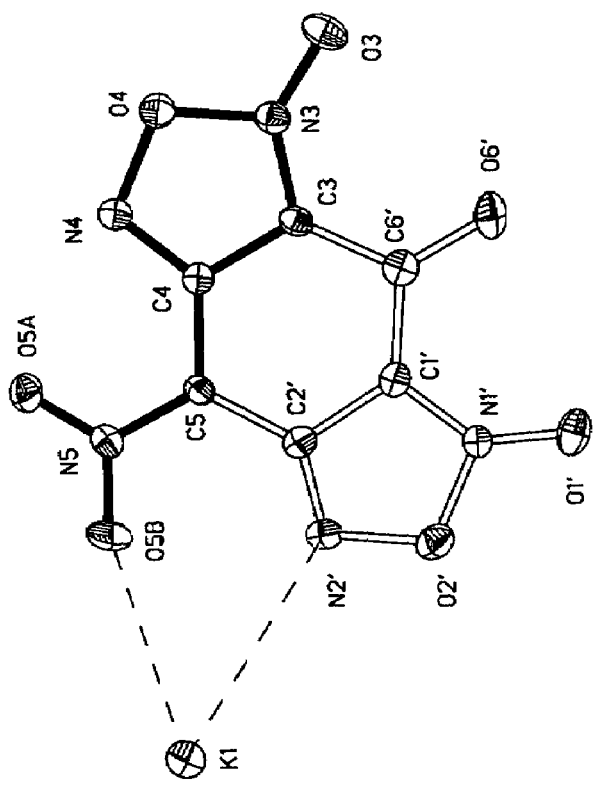
FIG. 1 illustrates Form A and Form B, hydroxynitrobenzodifuroxan, potassium salt of the present invention, with x-ray analysis of the respective structures.
Figure 1:
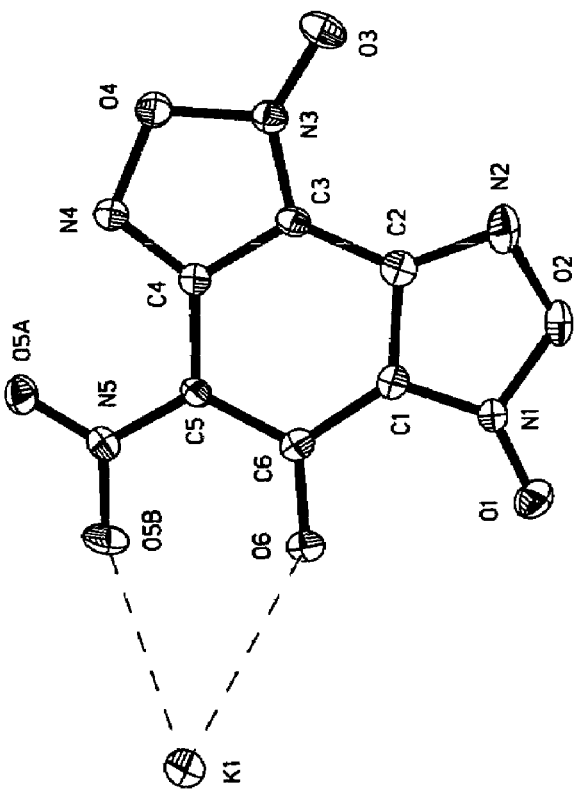

The present invention provides novel hydrolyzable and hydrolyzed nitrobenzodifuroxan materials, such as methoxynitrobenzodifuroxan and hydroxynitrobenzodifuroxan, including its salts, and methods of producing these materials. These nitrobenzodifuroxan compounds are useful in explosive compositions. Hydroxynitrobenzodifuroxan materials of the present invention include hydroxynitrobenzodifuroxan compounds and their salts. Metal salts of hydroxynitrobenzodifuroxan are particularly useful as sensitive explosives with high autoignition temperatures. The furoxan groups of the hydroxynitrobenzodifuroxan materials, in conjuction with the oxy-metal group, provide sensitivity. In addition, the oxy-metal group provides higher melting points and autoignition temperatures. As such, these hydroxynitrobenzodifuroxan materials are useful as lead azide and lead styphnate replacements in explosive compositions.

The present invention includes a nitrobenzodifuroxan compound having the chemical structure of:

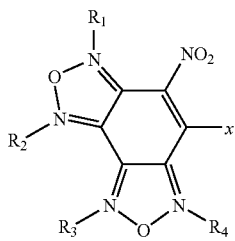

Formula I wherein $R_1$, $R_2$, $R_3$ and $R_4$ comprise oxygen or are absent, for a total of two oxygen atoms, and only one of $R_1$ or $R_2$ is present, and only one of $R_3$ and $R_4$ is present, and wherein x is a hydrolyzed or hydrolyzable substituent. Representative examples of x include OH, $OCH_3$, Cl, F, Br, OR, OC(O)R, where R comprises an alkyl group having from about 1 to about 3 carbon atoms, and other like units known to hydrolyze, combinations thereof, and other like substituents. Preferably, x comprises an OH group forming the hydroxynitrobenzodifuroxan, or an $OCH_3$ forming the methoxynitrobenzodifuroxan.

In a particularly preferred embodiment, the hydroxynitrobenzodifuroxan of the present invention comprises the hydroxynitrobenzodifuroxan salt. The hydroxynitrobenzodifuroxan salt is formed in Form A or Form B, as shown below.

Form A and Form B of the hydroxynitrobenzodifuroxan salt have the general chemical structure, below. In the general structures, two of the $R_1$, $R_2$, $R_3$ and $R_4$ comprise an oxygen atom, two are absent, and only one of $R_1$ or $R_2$ is present, and only one of $R_3$ and $R_4$ is present, and $Z^{\oplus}$ represents a cation.

General Structures

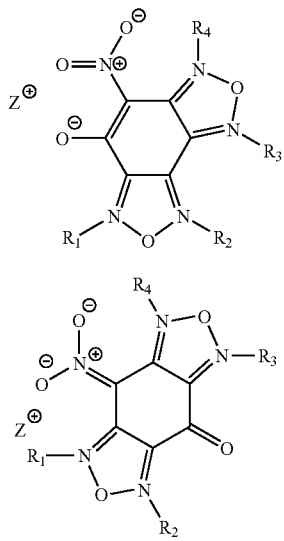

Form A

Form B

The preferred chemical structures of Form A and Form B of a potassium hydroxynitrobenzodifuroxan salt are shown below.

Specific Structures

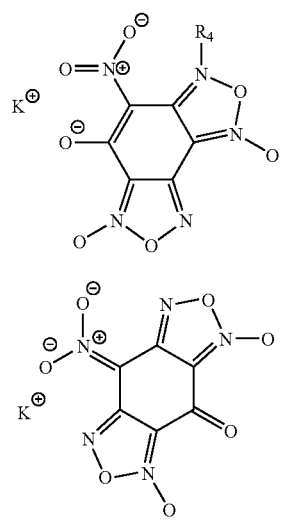

Form A

Form B

The hydroxynitrobenzodifuroxan salts of the present invention may include any appropriate salt, such as alkaline metal salts, other metal salts and amine salts. Representative alkaline metal salts include potassium, sodium, rubidium, lithium, cesium, magnesium, calcium, strontium, barium, etc., and combinations thereof, and the like. Additionally, representative other metal salts of the hydroxynitrobenzodifuroxan include cobalt (Co), copper (Cu), aluminum (Al), nickel (Ni), iron (Fe), titanium (Ti), antimony (Sb), zinc (Zn), zirconium (Zr), etc., combinations thereof, and the like. Preferred hydroxynitrobenzodifuroxan salts include potassium hydroxynitrobenzodifuroxan salts.

With acidic compounds, such as hydroxynitrobenzodifuroxan, other types of salts may also be formed, such as amine salts. Amine salts may have alternative uses such as propellant burning rate modifiers. Representative amine salts of the hydroxynitrobenzodifuroxan include $H_2NC(NH_2)NHCONH_2$, $C(NHNH_2)_3$, $NH_2NH_3$, $NH_4$, $H_2NNHC(NH_2)NH_2$, $(H_2NNH)_2C(NH_2)$, $C(NH_2)_3$, $(HONH_3)$, combinations thereof, and the like. Numerous heterocyclic amine salts of hydroxynitrobenzodifuroxan may also be formed and representative salts include salts from guanazole (3,5-diamino-1,2,4-triazole), 5-aminotetrazole, 3,6-dihydrazino-1,2-4,5-tetrazine, etc.

As seen in FIG. 1, an x-ray analysis is illustrated for Form A and Form B, hydroxynitrobenzodifuroxan, potassium salt of the present invention. A merged superposition of the two different anions was seen in the x-ray analysis, and each individual anion was mathematically extracted by modeling the image as a sum of two parts. The drawing shows the two different anion crystal structures ionically bonded to the potassium cation.

The present invention further includes the process for producing a hydrolyzable nitrobenzodifuroxan, such as methoxynitrobenzodifuroxan, and further processing a hydroxynitrobenzodifuroxan, and its salt. Generally, the formation of the hydrolyzable nitrobenzodifuroxan of the present invention, represented in Formula I, preferably includes the reaction sequence of:

(a) a tri-substituted trinitrobenzene, such as di-substituted trinitroanisole, is treated to produce a substituted diazidotrinitrobenzene (diazidotrinitroanisole); and, (b) the substituted diazidotrinitrobenzene (diazidotrinitroanisole) is treated to produce a substituted nitrobenzodifuroxan (methoxynitrobenzodifuroxan).

Generally, the formation of hydroxynitrobenzodifuroxan (represented by Formula I, above, with x being OH), and its salts, of the present invention preferably includes the reaction sequence of:

(c) the substituted nitrobenzodifuroxan, formed above, is hydrolyzed to produce hydroxynitrobenzodifuroxan; and, (d) with the formation of the hydroxynitrobenzodifuroxan, an additional step of converting the hydroxynitrobenzodifuroxan to its salt, such as by neutralization or by ion exchange reactions, may be done.

In the first step of forming the hydroxynitrobenzodifuroxan compound, the tri-substituted trinitrobenzene, preferably a di-substituted trinitroanisole, is used. In addition to the three nitro substituents on the benzo-structure, the trinitrobenzene includes two reactive sites for formation of $N_3$ substituents. Typical leaving groups at these two reactive sites may include, for example without limitation, chlorine, fluorine, bromine, iodine, nitro, etc. and combinations thereof. These leaving groups are removed with the application of an appropriate reactant, including treatment with an azide, such as sodium azide, trimethylsilyl azide, and combinations thereof. Preferably, the leaving group includes chlorine. Treatment of the trinitrobenzene forms $N_3$ substituents at the reactive sites to form the substituted diazidotrinitrobenzene.

The substituted diazidotrinitrobenzene is further treated to produce a nitrobenzodifuroxan, such as methoxynitrobenzodifuroxan, chloronitrobenzodifuroxan, fluoronitrobenzodifuroxan, etc, with methoxynitrobenzodifuroxan preferred. Hydrolyzation of this nitrobenzodifuroxan produces the hydroxynitrobenzodifuroxan.

Once formed, the hydroxynitrobenzodifuroxan may be further processed to form the hydroxynitrobenzodifuroxan salt. With the formation of the hydroxynitrobenzodifuroxan, an additional step of converting the hydroxynitrobenzodifuroxan to its salt, such as by neutralization or by ion exchange reactions, may be done. Representative neutralization reagents include metal hydroxides, metal oxides or amine bases, preferably with the aid of a solvent. Appropriate metal salts of weak acids, such as metal salts of acetic acid (potassium acetate, for example), may also be used as neutralization reagents. Representative ion exchange reactions include metal ion exchange by precipitation from solvent or metal ion exchange using an ion exchange resin.

Referring to Scheme 1A, below, the general reaction sequence is shown ($Y_1$ and $Y_2$ represent leaving groups, $Y_x$ represents a hydrolyzable substituent and $Z^{\oplus}$ represents a cation).

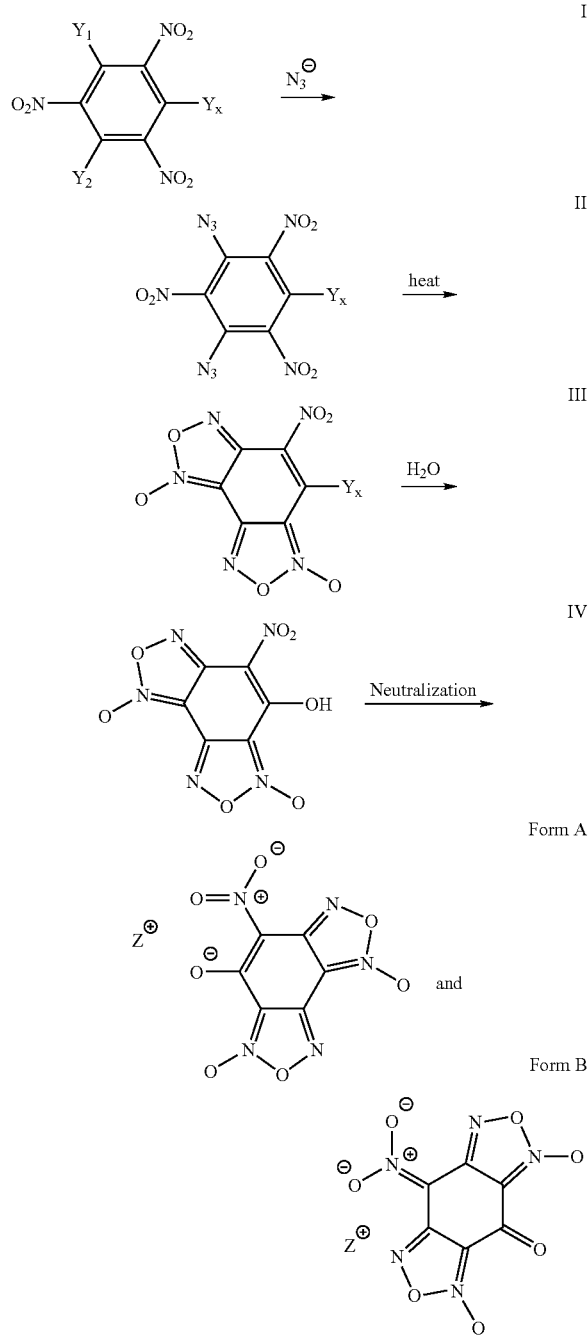

In a more specific embodiment of the general scheme (shown in Scheme 1A) for forming the hydroxynitrobenzodifuroxan, and its salts, of the present invention, formation is provided by the following reaction sequence (shown in Scheme 1B, below):

As seen in Scheme 1B, below, the reaction sequence includes:

(a) 3,5-dichloro-2,4,6-trinitroanisole is treated with sodium azide to produce 3,5-diazido-2,4,6-trinitroanisole, as exemplified in Example 1;

(b) the 3,5-diazido-2,4,6-trinitroanisole is heated in an appropriate solvent to produce methoxynitrobenzodifuroxan, as exemplified in Example 2;

(c) the methoxynitrobenzodifuroxan is hydrolyzed to produce hydroxynitrobenzodifuroxan, as exemplified in Example 3; and, (d) hydroxynitrobenzodifuroxan is converted to salts by neutralization, as exemplified in Examples 4 and 5, or by ion exchange reactions.

EXAMPLE 1

Preparation of 3,5-diazido-2,4,6-trinitroanisole

A solution of 3,5-dichloro-2,4,6-trinitroanisole (1.50 g, 4.8 mmol) in dimethyl carbonate (15 mL) was stirred in a 100 mL one-neck round-bottomed flask. A solution of tetrabutylammonium bromide in water (4.4 mL) was added. [The solution of tetrabutylammonium bromide was prepared by dissolving it (0.30 g) in distilled water (30 mL) and using 4.4 mL of this solution]. A solution of sodium azide (0.90 g, 13.8 mmol) in distilled water (18 mL) was then added. The flask was stoppered and the mixture was stirred vigorously at room temp for 22 hr.

At this point, thin layer chromatography (TLC) was performed. TLC (using toluene/heptane 50/50 by volume as developer) of a small sample of the lower layer (diluted with acetone) indicated the reaction was complete ($R_F$ of diazido-product and the starting material are 0.46 and 0.62, respectively; note that the diazido product turns yellow after standing on the TLC plate). The lower yellow layer was separated and the upper aqueous phase was extracted with dimethyl carbonate (3×5 mL). The yellow layer and extracts were combined. TLC and $^1$H NMR analyses indicated the dimethyl carbonate solution contained essentially pure 3,5-diazido-2,4,6-trinitroanisole. $^1$H NMR (acetone-$d_6$): 4.11 (s).

EXAMPLE 2

Preparation of Methoxynitrobenzodifuroxan

The volatiles from the combined dimethyl carbonate yellow layer/extracts, from Example 1 above, were cautiously removed (without heating above room temperature) until the remaining volume of dimethyl carbonate was 10 mL. Toluene (40 mL) was added and the toluene/dimethyl carbonate solution was dried over anhydrous sodium sulfate overnight. The sodium sulfate was removed by filtration and the filter cake was washed with toluene (3×7 mL). The filtrate was heated in an oil bath near 100° C. for 7 hr. After 4.5 hr, TLC (toluene as developer) showed a small amount of the starting diazido compound. (The $R_F$ of methoxynitrobenzodifuroxan is about 0.64; the $R_F$ of the starting diazido compound is 0.77; the methoxynitrobenzodifuroxan product leaves a trail from the origin on the TLC plate, presumably due to hydrolysis.)

The reaction solution was allowed to cool to room temperature and stand overnight before the solution was decanted from a small amount (0.03 g) of a dark precipitate. The volatiles were cautiously removed (without heating above room temperature) to give 1.39 g of residue (mostly solid with some oil). The residue was stirred with chloroform (10 mL) at room temperature to give insoluble crystals. The mixture was cooled at 5° C. for 1 hr and then at −15° C. for 30 min before the crystals were removed and washed with cold (−15° C.) chloroform. The yellow-brown crystals weighed 0.60 g, mp 149–152° C. A second crop gave an additional 0.11 g (mp 140–145° C.) of yellow-brown crystals. The yield of crystalline methoxynitrobenzodifuroxan was about 55%. $^1$H NMR (DMSO-$d_6$, contains some absorbed H$_2$O): singlets (OCH$_3$) at 3.99, 4.19, 4.49 and 4.54 that vary in intensity over time; after 22 hr, only the peak at 3.99 remains; also a peak of increasing intensity at 3.18 (methanol) and broader peaks between 3.5 to 4.9 (H$_2$O/OH). These results indicate that the methoxynitrobenzodifuroxan is undergoing rearrangements (to form furoxan isomers) and also is undergoing hydrolysis. $^1$H NMR (dry acetone-$d_6$): singlets (OCH$_3$) at 4.28, 4.59 and 4.63. IR (KBr): 1685, 1585, 1528, 1352, 1297, 1087, 999, 769 cm$^{-1}$.

EXAMPLE 3

Preparation of Hydroxynitrobenzodifuroxan

Methoxynitrobenzodifuroxan (0.30 g, mp 149–152° C.), prepared as in Example 2 above, was dissolved by stirring in acetone (10 mL). Distilled water (2 mL) was added. (Some product precipitated from solution when the water was added, but re-dissolved as the mixture was heated towards 52–54° C.) The solution was held near 55° C. for 1.7 hr during which time it turned dark red brown. The volatiles were cautiously removed (without heating above room temperature) to give a red-brown solid (0.34 g), which was then stirred in distilled water (5 mL) at room temperature. A very small amount (0.01 g) of insoluble yellow solid was removed by filtration and washed with of distilled water (2×1.5 mL). The volume of the filtrate was 8 mL. The water was removed from one mL of the filtrate (without heating above room temperature) to give a light red solid, which had a melting point of 95° C. (with vigorous decomposition).

EXAMPLE 4

Preparation of Hydroxynitrobenzodifuroxan, Potassium Salt

The remainder of the filtrate (7 mL) from Example 3 above was stirred at room temperature while potassium carbonate (0.16 g) was slowly added in portions. Crystals precipitated as the solution was neutralized. The mixture was cooled to 5° C. and the deep red-brown crystals were removed and washed with ice-cold water (3×1.5 mL). The red-brown crystals were air dried to give hydroxynitrobenzodifuroxan, potassium salt (0.18 g, 63% yield based on methoxynitrobenzodifuroxan). The red-brown crystals explode in the vicinity of 200° C. $^{13}$C NMR (D$_2$O): 110.9, 140.1, 149.8, 150.9 162.8, 163.0 (The D$_2$O solution was prepared at 60° C.; then cooled to room temperature without precipitation from solution). $^{13}$C NMR (DMSO-$d_6$): 97.2, 99.4, 101.8, 105.9, 110.0, 114.9, 116.4, 140.3, 150.1, 151.0, 151.5, 159.3, 160.6, 161.7 [The numerous peaks in DMSO-$d_6$ are presumably due to furoxan isomers that form in solution. Complete removal of the DMSO-$d_6$ solvent under reduced pressure gave a red-brown crystalline residue that behaves as the original crystals (explodes in the vicinity of 200° C.)]. IR (total attenuated reflectance): 1698, 1648, 1574, 1549, 1460, 1359, 1337, 1277 (very strong), 1236, 1217, 1081, 970, 938, 891, 800, 759 cm$^{-1}$.

Crystal structure analysis showed that the red-brown crystals contain two forms, Form A and Form B, of the hydroxynitrobenzodifuroxan, potassium salt (shown in FIG. 1), in approximately equal amounts. Differential scanning calorimetry (DSC) showed the potassium salt to have an autoignition temperature of approximately 200° C. (at a heating rate of 20° C. per minute).

Scheme 1B

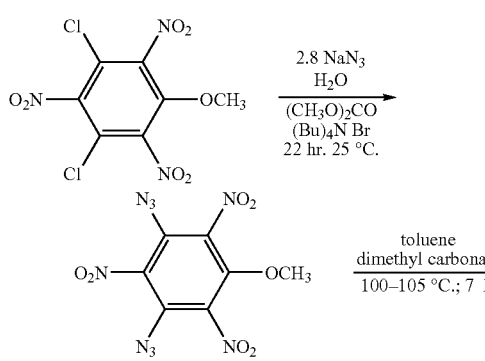

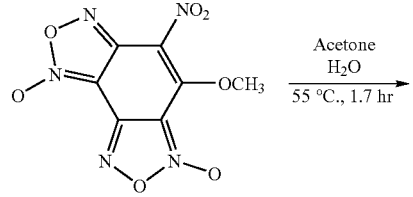

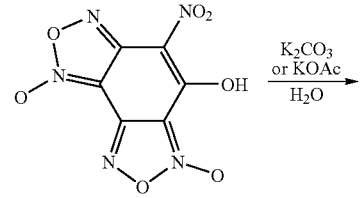

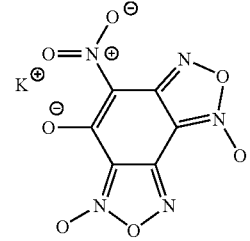

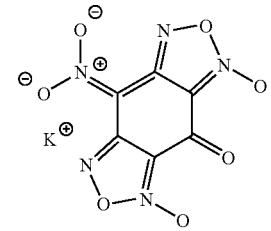

EXAMPLE 5

Preparation of Hydroxynitrobenzodifuroxan, Rubidium Salt

A solution containing hydroxynitrobenzodifuroxan (0.34 g) in water (8 mL) was stirred at room temperature while aqueous rubidium hydroxide solution was slowly added to raise the pH to 7 to 8 (by pH paper) and form a dark brown crystalline precipitate. [The aqueous rubidium hydroxide solution was prepared by diluting 0.6 g of a 50 wt. % aqueous solution of rubidium hydroxide with water (2 mL); about 1 mL of the diluted solution was required for the neutralization.] The mixture was cooled to 5° C. for 30 minutes before the crystals were removed and washed with ice-cold water (3×1 mL). The first crop gave 0.11 g of dark red-brown crystals. Concentration of the filtrate gave a second crop (0.02 g), raising the total yield to 0.13 g (31%). The crystals explode in the vicinity of 200° C., in very similar manner to the potassium salt.

In a less preferred embodiment, the hydroxynitrobenzodifuroxan, and its salts, of the present invention include formation provided by the reaction sequence using a trichlorotrinitrobenzene. This was difficult to control after substitution of the first two chlorine leaving groups, as the replacement of the third chlorine atom readily occurred once replacement of the first two chlorine atoms had occurred. As such, it is expected that other reactants having identical substituents in the three locations may experience similar control issues.

The present invention also addresses a need for thermally stable primary initiating explosives that are sensitive to laser initiation, i.e., a need for primary explosives that will initiate by absorbing laser-emitted light. As the hydroxynitrobenzodifuroxan, potassium salt has absorptions at 500 and 400 nm, the compound may be tailored to specialized initiation procedures. This ability to absorb light indicates that salts of hydroxynitrobenzodifuroxan are potentially useful as laser sensitive initiating materials.

The foregoing summary, description, and examples of the present invention are not intended to be limiting, but are only exemplary of the inventive features that are defined in the claims.

What is claimed is:

1. A nitrobenzodifuroxan compound consisting of a chemical structure:

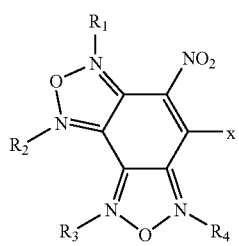

wherein two of $R_1$, $R_2$, $R_3$ and $R_4$ consist of oxygen, for a total of two oxygen atoms so that only one of $R_1$ and $R_2$ is present as said oxygen, and only one of $R_3$ and $R_4$ is present as said oxygen, and wherein x is one of a hydrolyzed substituent and a hydrolyzable substituent.

2. The compound of claim 1, wherein x is selected from OH, Cl, F, Br, and OR, where R is an alkyl group consists of from about 1 to about 3 carbon atoms.

3. The compound of claim 1, wherein x is selected from OH and $OCH_3$.

4. The compound of claim 3, wherein said nitrobenzodifuroxan compound is a methoxynitrobenzodifuroxan compound.

5. The compound of claim 1, wherein said nitrobenzodifuroxan compound is a hydroxynitrobenzodifuroxan compound.

6. A hydroxynitrobenzodifuroxan compound, including a salt thereof, consisting of a chemical structure:

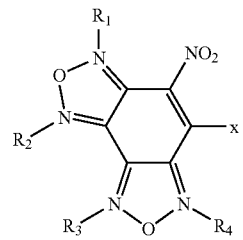

wherein two of $R_1$, $R_2$, $R_3$ and $R_4$ consist of oxygen for a total of two oxygen atoms so that only one of $R_1$ and $R_2$ is present as said oxygen, and only one of $R_3$ and $R_4$ is present as said oxygen and wherein x is an OH substituent.

7. The hydroxynitrobenzodifuroxan compound of claim 6, consisting of a salt of hydroxynitrobenzodifuroxan compound.

8. The hydroxynitrobenzodifuroxan compound of claim 7, consisting of Form A of hydroxynitrobenzodifuroxan salt.

9. The hydroxynitrobenzodifuroxan of claim 7, consisting of Form B of hydroxynitrobenzodifuroxan salt.

10. The hydroxynitrobenzodifuroxan compound of claim 7, wherein the salt of said hydroxynitrobenzodifuroxan compound is selected from alkaline metal salts, other metal salts and amine salts.

11. The hydroxynitrobenzodifuroxan compound of claim 7, wherein said salt of said hydroxynitrobenzodifuroxan compound is an alkaline metal salt selected from at least one of potassium, sodium, rubidium, lithium, cesium, magnesium, calcium, strontium, and barium.

12. The hydroxynitrobenzodifuroxan compound of claim 7, wherein said salt of said hydroxynitrobenzodifuroxan compound is an amine salt selected from at least one of $H_2NC(NH_2)NHCONH_2$, $C(NHNH_2)_3$, $NH_2NH_3$, $NH_4$, $H_2NNHC(NH_2)NH_2$, $(H_2NNH)_2C(NH_2)$, $C(NH_2)_3$, and $(HONH_3)$.

13. The hydroxynitrobenzodifuroxan compound of claim 7, wherein said salt of said hydroxynitrobenzodifuroxan compound is a metal salt selected from at least one of cobalt (Co), copper (Cu), aluminum (Al), nickel (Ni), iron (Fe), titanium (Ti), antimony (Sb), zinc (Zn), and zirconium (Zr).

* * * * *